United States Patent [19]

Moreau et al.

[11] 4,003,931
[45] Jan. 18, 1977

[54] DERIVATIVES OF ALPHA-METHYL BENZYLAMINE

[75] Inventors: Michèle Moreau; Isaac Karadavidoff, both of Paris; Claude Rissé, Saint-Michel-sur-Orge, all of France

[73] Assignee: Fuveau S.A., Paris, France

[22] Filed: Oct. 27, 1971

[21] Appl. No.: 193,175

[30] Foreign Application Priority Data

Oct. 28, 1970 France .............................. 70.38818
July 15, 1971 France .............................. 71.25902

[52] U.S. Cl. .................... 260/570.5 P; 260/465 E; 260/501.1; 260/562 R; 260/570.8 R; 260/592; 260/618 R; 424/304; 424/316; 424/330
[51] Int. Cl.² ........................................ C07C 87/28
[58] Field of Search ................... 260/570.8

[56] References Cited

UNITED STATES PATENTS

| 3,448,106 | 6/1969 | Nickl et al. ................ 260/570.9 X |
| 3,520,931 | 7/1970 | d'Ostrowick et al. .......... 260/570.8 |
| 3,639,423 | 2/1972 | Winter et al. .............. 260/570.9 X |

OTHER PUBLICATIONS

Roocker et al., "Chemical Abstracts," vol. 59, pp. 9845–9846 (1963).

*Primary Examiner*—Robert V. Hines
*Attorney, Agent, or Firm*—Fitzpatrick, Cella, Harper & Scinto

[57] ABSTRACT

New amines having an anti-inflammatory and analgesic activity, represented by the formula:

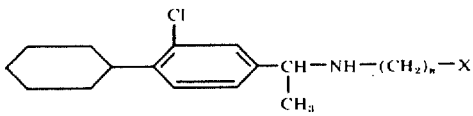

in which X represents a hydrogen or halogen atom such as chlorine, a cyanide or amino group of the formula

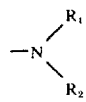

in which $R_1$ and $R_2$ are each a hydrogen atom, or a lower alkyl group, or form with the nitrogen atom a saturated or unsaturated heterocyclic group at $C_5$ or $C_6$ which may contain a second hetero atom such as oxygen or nitrogen, $n$ is equal to 1, 2 or 3 and may be equal to 0 when X represents a hydrogen atom, and their addition salts of pharmaceutically acceptable acids.

Method of preparing the above compounds from 3-chloro 4-cyclohexyl acetophenone, which is transformed into 3-chloro 4-cyclohexyl α-methyl benzylamine, which is then condensed with an amine of the formula $X-(CH_2)n - NH_2$, in which X and $n$ are above defined.

5 Claims, No Drawings

DERIVATIVES OF ALPHA-METHYL BENZYLAMINE

The present invention relates to new derivatives of α methyl benzyl amine having an anti-inflammatory and analgesic action, which are shown by the following general formula:

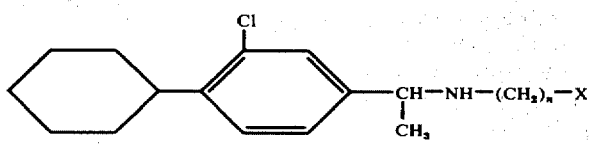

(I)

in which X represents a hydrogen atom or a halogen atom such as chlorine, a cyanide group or amine group of formula

in which $R_1$ and $R_2$ are each, either a hydrogen atom or a lower alkyl group, or form with the nitrogen atom a saturated or unsaturated heterocyclic group at $C_5$ or $C_6$ which can contain a second hetero atom such as oxygen or nitrogen, n is equal to 1, 2 or 3, and may be equal to 0 when X represents a hydrogen atom; and their addition salts of pharmaceutically acceptable acids.

The new compounds according to the invention are prepared usually from 3-chloro 4-cyclohexyl acetophenone. The ketone function of the latter is reduced by sodium boro-hydride, to a secondary alcohol; and, by chlorination of this alcohol by thionyl chloride in a benzene solvent at a temperature between 0 and 80° C the intermediate compound of the following formula is obtained:

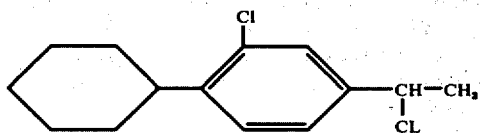

(II)

By the reaction of this intermediate compound (II) with an amine of formula $X(CH_2)_n$—$NH_2$, in which n is as defined above, and X is a hydrogen or chlorine atom, or a

group as defined above, the corresponding compounds of formula (I) are obtained.

In order to obtain the compound of formula I, in which n=2 and X is a cyanide group, the compound of formula (I), obtained previously, in which n=0 and X is a hydrogen atom, is then reacted with acrylonitrile by heating under reflux for 8 – 24 hours.

A preferred method for preparing the compound of formula I according to the invention, in which n=0 and X is a hydrogen atom, is to react ammonium formate with 3-chloro 4-cyclohexyl acetophenone at a temperature of the order of 170°–200° C, and then to hydrolyze the derivative obtained by the addition of hydrochloric acid.

According to the operative conditions, the compound is obtained in the uncombined form, or in the form of its salts, which, in the usual manner, can be mutually converted one to the other or into other salts. These chosen salts will be those obtained by the addition of therapeutically acceptable mineral or organic acids, for example, hydrochloride, oxalate, succinate.

Another preferred method for preparing the compound of formula I according to the invention, in which n=1 and X is a hydrogen atom, consists of a reductive amination of the starting material 3-chloro 4-cyclohexyl acetophenone by methylamine. This reaction is carried out in an autoclave under a hydrogen pressure of about 1–5 kg/cm² in the presence of a hydrogenation catalyst such as platinum oxide.

The following examples are intended to illustrate the invention without restricting it.

EXAMPLE 1

Preparation of the Intermediate Compound of Formula II (3-chloro 4-cyclohexyl α-chloro ethylbenzene)

2.9 gms. of sodium boro-hydride in 60 ml. of water, is added to 13 gms. of 3-chloro 4 cyclohexyl acetophenone in 230 ml of methyl alcohol (methanol), over a period of 45 minutes at a temperature between 20°–28° C. It is left for 3 hours at ambient temperature and is stirred. After evaporation and then the addition of water, it is extracted with ether, washed and dried. The distilled product reaches the B. Pt. 145°–150° C under a pressure of 2.5 mm Hg. 10 gms. of 3 chloro 4-cyclohexyl -α-hydroxy ethylbenzene are obtained.

Then the chlorination reaction is carried out by the addition of 41 ml of $SO_2 Cl_2$ in 20 ml of benzene to a solution of 10 gms. 3-chloro 4-cyclohexyl α-hydroxy ethylbenzene in 50 ml of benzene, over a period of 30 minutes at 10° C. The mixture is refluxed for 24 hours, then it is evaporated to dryness and distilled at the B.P. 148°–155° C under a pressure of 2.5 mmHg. 9gm of the desired product are obtained (yield 84%).

EXAMPLE 2

Preparation of the Hydrochloride of N-ethyl 3-chloro cyclohexyl α-methyl benzylamine 20 ml of pure ethylamine (cooled to −10° C) is added to 10 gms of the compound, prepared in example 1, in 20 ml of benzene, and is refluxed for 48 hours. After evaporation to dryness, it is dissolved in water and extracted with ether. It is washed, dried and after the addition of hydrochloric acid 6.4 gm of hydrochloride is obtained which is recrystallised from isopropanol, MP : 210° C.

EXAMPLE 3

Preparation of the Hydrochloride of N-dimethyl amino-ethyl 3-chloro 4-cyclohexyl -αmethyl benzylamine 20 ml of dimethyl amino-2 ethyl amine is added to a solution of 9 gms of the compound, described in example 1, in 40 ml of toluene. It is refluxed for 48 hours. After evaporation to dryness and addition of water, it is extracted with ether, washed and dried in order to obtain an oil. The dihydrochloride is obtained by the addition of hydrochloric ether, i.e. 6.25 g. (yield 59.5%) of the desired product after recrystallisation from ethyl alcohol (ethanol) MP : 247° C.

EXAMPLE 4

Preparation of the Hydrochloride of Nα-dimethyl 3-chloro 4-cyclohexyl benzylamine A solution of 9.5 gms. of 3-chloro 4-cyclohexyl acetophenone in 86 ml of ethyl alcohol (ethanol), 11 ml of 34% methylamine, and 100 ml of $Pto_2$ is put into an autoclave under hydrogen pressure (about 5kg/cm$^2$), it is stirred at ambient temperature for 6 hours. After eliminating the catalyst, the solution is evaporated to dryness and an oil is obtained which is mixed with hydrochloric acid with a view to obtaining the hydrochloride.

After washing with ether and drying, 5.72 gms of the desired product are obtained, i.e. a yield of 52% — MP : 198° C.

EXAMPLE 5

Preparation of 3-chloro 4-cyclohexyl α-methyl benzylamine

A mixture of 10 gms of 3-chloro 4-cyclohexyl acetophenone is heated, in a metallic bath, with 13.25 gms of ammonium formate, a yellow straw-coloured homogeneous solution is obtained, accompanied by a high liberation of ammonia.

The temperature is raised to 210° C and it is left for a few hours. 5 ml of formamide is added and the heating is stopped. After the addition of water to the solution, it is extracted with benzene, washed with water and evaporated to dryness in order to obtain a brown oil which is mixed with 25 ml of concentrated HCl. It is refluxed for 4 hours; the hydrochloride of the desired product precipitates; it is isolated by filtering and washed with ethyl acetate; the product becomes white and finely crystallised. Several recrystallizations from isopropanol methyl-ethyl-ketone mixture are necessary.

6.67 gms of the hydrochloride of 3-chloro 4-cyclohexyl α-methyl benzylamine are obtained whose melting point is 240° C (with decomposition).

| Analysis: | |
|---|---|
| inorganic chlorine | : 12.96% (Calculated) 15.10% (found) |
| total chlorine | : 25.91% (Calculated) 26.15% (found) |
| Nitrogen | : 5.11% (Calculated) 5.11% (found) |

In order to obtain the amine in the free form, the operation is carried out in the usual manner, by adding a mixture of water and 10% soda, the product is made soluble, it is extracted with ether and dried on sodium sulphate, and is isolated by filtration and evaporation, the amine is in the form of an oil.

EXAMPLE 6

Preparation of the Hydrochloride of N-cyanoethyl-3-chloro 4-cyclohexyl-α-methyl benzyl=amine 20 ml of acrylonitrile are added to 13 gms of 3-chloro 4-cyclohexyl-α-methyl benzylamine and are refluxed for 8 hours. The excess acrylonitrile is evaporated and distilled. The product reaches a B.Pt. of 180°–185° C at a pressure of 1mmttg.

By the addition of hydrochloric acid 11 gms of hydrochloride are obtained which are recrystallised from ethyl alcohol (ethanol) m.p. .255° C. The pharmacological study of the new derivatives of α-methyl benzylamine of formula I has shown particularly advantageous anti-inflammatory and analgesic properties.

The anti-inflammatory action has been studied on the edema of the foot of a mouse with carrageenin by the technique of Winter S.A. (Proc. Soc. Exp. Biol. Med. 1962, 111 544). It has been found, that the derivatives of the invention, administered with doses ranging from 90–180 mg/kg per bone, inhibit the inflammatory reaction by the order of 30–60%.

The analgesic action is determined by the method with acetic acid on mice (test of Koster R. Coll, Fed. Proc. 1959, 18, 412). It has been established that these derivatives inhibit the painful reaction by 30–85% (percentage expressed by the reduction of the number of contortions of the animal treated with respect to those not treated, determined 10 minutes after the acid injection,) with doses rising from 60–120 mg/kg per bone.

The new derivatives of α-methyl benzyamine proved to be very useful in the treatment of inflammatory outbreakes of any origin.

For use in man as new anti-inflammatory and analgesic medicines, for example, in the treatment of arthritis and various rheumatic disorders the total dose recommended is from 100–1000 mg every 24 hours, according to the sensitivity of the patient.

The compounds according to the invention, are administered to the patients in the form of pharmaceutical compounds in which they are associated with an acceptable pharmaceutical medium, suitable orally or parenterally, the unitary dose of active product being from 50–500 mg.

What is claimed is:

1. Compounds of formula:

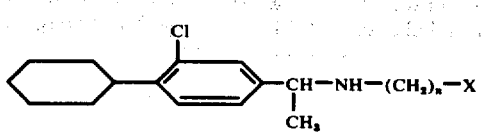

in which X is hydrogen, halogen or an amine group of the formula $$-N\begin{matrix}R_1\\R_2\end{matrix}$$

in which $R_1$ and $R_2$ are each hydrogen or a lower alkyl group, $n$ is equal to 1, 2, or 3 and may equal 0 when X is hydrogen and their addition salts of pharmaceutically acceptable acids.

2. Compound according to claim 1, in which $n=0$ and X is a hydrogen atom, and which is the 3-chloro-4-cyclohexyl α-methyl benzylamine or its addition salts of pharmaceutically acceptable acids.

3. Compound according to claim 1, in which $n=1$ and X is a hydrogen atom and which is the N, α-dimethyl 3-chloro-4-cyclohexyl benzylamine or its addition salts of pharmaceutically acceptable acids.

4. Compound according to claim 1, in which $n=2$ and X is a hydrogen atom and which is the N-ethyl 3-chloro 4-cyclohexylα-methyl benzylamine or its addition salts of pharmaceutically acceptable acids.

5. Compound according to claim 1, in which $n=2$ and X is a dimethyl amino - ethyl 3-chloro 4-cyclohexylα-methyl benzylamine or its addition salts of pharmaceutically acceptable acids.

* * * * *